(12) United States Patent
Barrus et al.

(10) Patent No.: US 8,377,101 B2
(45) Date of Patent: Feb. 19, 2013

(54) MULTI-PLANAR TAPER LOCK SCREW WITH INCREASED ROD FRICTION

(75) Inventors: Michael Barrus, Ashburn, VA (US); Mary P. Hamburger, Herndon, VA (US)

(73) Assignee: K2M, Inc., Leesburg, VA (US)

( * ) Notice: Subject to any disclaimer, the term of this patent is extended or adjusted under 35 U.S.C. 154(b) by 527 days.

(21) Appl. No.: 12/612,759

(22) Filed: Nov. 5, 2009

(65) Prior Publication Data
US 2010/0114170 A1 May 6, 2010

Related U.S. Application Data

(60) Provisional application No. 61/198,385, filed on Nov. 5, 2008.

(51) Int. Cl.
*A61B 17/70* (2006.01)
(52) U.S. Cl. .................................. 606/264; 606/272
(58) Field of Classification Search ............ 606/246, 606/59, 264
See application file for complete search history.

(56) References Cited

U.S. PATENT DOCUMENTS

| | | | |
|---|---|---|---|
| 5,738,685 A | 4/1998 | Halm et al. | |
| 5,885,286 A | 3/1999 | Sherman et al. | |
| 6,074,391 A | 6/2000 | Metz-Stavenhagen et al. | |
| 6,110,172 A * | 8/2000 | Jackson | 606/305 |
| 6,132,434 A | 10/2000 | Sherman et al. | |
| 6,254,602 B1 | 7/2001 | Justis | |
| 6,273,888 B1 | 8/2001 | Justis | |
| 6,296,642 B1 | 10/2001 | Morrison et al. | |
| 6,302,888 B1 | 10/2001 | Mellinger et al. | |
| 6,827,719 B2 | 12/2004 | Ralph et al. | |
| 6,835,196 B2 | 12/2004 | Biedermann et al. | |
| 6,837,889 B2 | 1/2005 | Shluzas | |
| 6,843,791 B2 | 1/2005 | Serhan | |
| 6,869,433 B2 | 3/2005 | Glascott | |
| 6,884,244 B1 | 4/2005 | Jackson | |
| 6,893,443 B2 | 5/2005 | Frigg et al. | |
| 6,896,677 B1 | 5/2005 | Lin | |
| 6,918,911 B2 | 7/2005 | Biedermann et al. | |
| 6,945,975 B2 | 9/2005 | Dalton | |
| 7,087,057 B2 * | 8/2006 | Konieczynski et al. | 606/278 |
| 7,445,627 B2 * | 11/2008 | Hawkes et al. | 606/269 |
| 2002/0032443 A1 * | 3/2002 | Sherman et al. | 606/61 |
| 2006/0173456 A1 | 8/2006 | Hawkes et al. | |
| 2006/0217715 A1 * | 9/2006 | Serhan et al. | 606/61 |
| 2006/0271047 A1 | 11/2006 | Jackson | |
| 2006/0276792 A1 | 12/2006 | Ensign et al. | |
| 2007/0093817 A1 | 4/2007 | Barrus et al. | |

* cited by examiner

*Primary Examiner* — Eduardo C Robert
*Assistant Examiner* — James Palmer
(74) *Attorney, Agent, or Firm* — Carter, DeLuca, Farrell & Schmidt, LLP

(57) ABSTRACT

A spinal fixation device includes a coupling, a pedicle screw, and a collet. The coupling has an opening extending therethrough. The pedicle screw has a head mounted to a shank that is positionable within a first vertebral body. The collet is receivable in the opening of the coupling and engagable with the head of the pedicle screw. The collet is selectively positionable between a first position and a second position where the collet engages a spinal rod and prevents one or both of axial and rotational movement of the spinal rod. The collet is adapted to facilitate the connection of the spinal rod to a second vertebral body. The collet defines a saddle having one or more locking features for engaging the spinal rod.

18 Claims, 10 Drawing Sheets

MULTI-PLANAR TAPER LOCK SCREW WITH INCREASED ROD FRICTION

CROSS-REFERENCE TO RELATED APPLICATIONS

This application claims priority to, and the benefit of, U.S. Provisional Patent Application Ser. No. 61/198,385, filed Nov. 5, 2008, the contents of which are hereby incorporated by reference in their entirety.

BACKGROUND

1. Technical Field

The present disclosure relates generally to orthopedic surgery and in particular to devices and prosthesis for stabilizing and fixing the bones and joints of the body.

2. Background of Related Art

It is a common surgical procedure to stabilize and fix bones and bone fragments in a particular spatial relationship with fixation devices to correct the location of skeletal components due to injury or disease. This can be accomplished by using a number of fixation devices such as bone pins, anchors, or screws placed in bone across a discontinuity (e.g., a fracture) in the bone, bone fragments, adjacent vertebrae, or joints. These fixation devices can be connected by a rod to maintain a desired spatial relationship. In some cases, these fixation devices may be permanently implanted. In other cases, these fixation devices may be implanted only as a temporary means of stabilizing or fixing the bones or bone fragments. It is also common that fixation devices that are intended to be permanently implanted require subsequent modifications as the dynamics of a patient's condition warrant.

Spinal fixation devices are widely employed in surgical processes for correcting spinal injuries and diseases. These devices commonly employ longitudinal link rods (e.g., spinal rods) secured to vertebrae by spinal bone fixation fasteners such as pedicle screws, hooks and others.

Many conventional devices for locking a spinal rod to a hook or screw do not offer the needed flexibility to allow the spinal rod to be easily connected to misaligned adjacent vertebrae. In addition, the spinal rod may excessively rotate and/or axially translate when being positioned within the screw, making the spinal rod securement even more difficult. Some effort has been made to provide a multi-planar screw; however, even for devices that have attempted to address the issue of securing spinal rods to misaligned vertebrae, there remains the problem of providing such a multi-planar screw and spinal rod combination that can be easily locked and unlocked in position without the need to exert additional torque to the device or force on the patient. Furthermore, it would be desirous to provide a multi-planar screw and spinal rod combination having increased friction therebetween, such that when the spinal rod and the multi-planar screw are engaged, axial and/or rotational movement of the spinal rod is prevented. This will facilitate the spinal rod securement.

SUMMARY

The present disclosure relates to a spinal fixation device including a coupling, a pedicle screw, and a collet. The coupling has an opening extending therethrough. The pedicle screw has a head mounted to a shank that is positionable within a first vertebral body. The collet is receivable in the opening of the coupling and engagable with the head of the pedicle screw. The collet is selectively positionable between a first position and a second position where the collet engages a spinal rod and prevents at least one of axial and rotational movement of the spinal rod. The collet is adapted to facilitate the connection of the spinal rod to a second vertebral body misaligned with respect to the first vertebral body. The collet may be adapted to facilitate the connection of the spinal rod to a second vertebral body misaligned with respect to the first vertebral body when the collet is in the second position. The collet defines a saddle having one or more locking features for engaging the spinal rod. The one or more locking features may define a scalloped surface. The one or more locking features may include a slot defined within the surface of the saddle. In one embodiment, two or more locking features are defined within the surface of the saddle and each locking feature has a radius defined by a center point, wherein the center points are non-coincidental. The collet may include one or more relief slots. The collet may include an upper portion and a lower portion, wherein the one or more relief slots are disposed within one or both of the upper portion and the lower portion. The one or more locking features include one or both of a flat edge or a corner. In embodiments, the saddle of the collet includes surface texturing.

In one aspect, a spinal fixation assembly includes a spinal rod having at least one flat surface and a spinal fixation device. The spinal fixation device includes a coupling, a pedicle screw and a collet. The coupling has an opening extending therethrough. The pedicle screw has a head mounted to a shank. The shank is positionable within a first vertebral body. The collet is receivable in the opening of the coupling and engagable with the head of the pedicle screw. The collet is selectively positionable between a first position and a second position where the collet engages a spinal rod and prevents at least one of axial and rotational movement of the spinal rod. The collet is adapted to facilitate the connection of the spinal rod to a second vertebral body misaligned with respect to the first vertebral body. The collet defines a saddle having one or more locking features for engaging the one or more flat surfaces of the spinal rod.

The spinal fixation assembly further includes a second spinal fixation device positionable within the second vertebral body and engagable with the spinal rod.

In another aspect, a method for mounting a spinal fixation assembly includes providing a spinal fixation assembly including a spinal rod having one or more flat surfaces and a first spinal fixation device including a coupling having an opening extending therethrough; a pedicle screw having a head mounted to a shank, the shank positionable within a first vertebral body; and a collet receivable in the opening of the coupling and engagable with the head of the pedicle screw, the collet selectively positionable between a first position and a second position where the collet engages a spinal rod and prevents at least one of axial and rotational movement of the spinal rod, the collet adapted to facilitate the connection of the spinal rod to a second vertebral body misaligned with respect to the first vertebral body, the collet defining a saddle having one or more locking features for engaging the one or more flat surfaces of the spinal rod; and a second spinal fixation device.

The method includes mounting the first spinal fixation device to the first vertebral body, mounting the spinal rod to the first spinal fixation device, locking the spinal rod to the first spinal fixation device, mounting the second spinal fixation device to the second vertebral body where the second vertebral body is misaligned with the first vertebral body, and mounting the spinal rod to the second spinal fixation device.

One step includes locking the one or more flat surfaces of the spinal rod with the one or more locking features of the saddle of the collet of the first spinal fixation device. The method includes the step of locking the spinal rod to the second spinal fixation device where the second spinal fixation device includes a collet having a saddle defining one or more locking features engagable with the one or more flat surfaces of the spinal rod.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION OF THE EMBODIMENTS

Figure 1C:
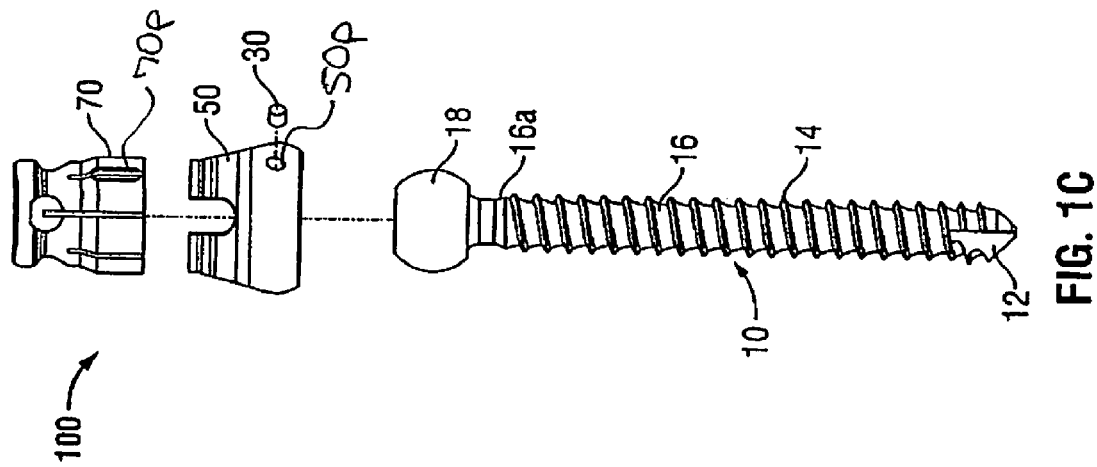
FIG. 1C is an exploded side view of the spinal fixation device of FIG. 1A with parts separated illustrating a pedicle screw, a coupling, a collet, and a pin.

Various embodiments of the presently disclosed spinal fixation device will now be described in detail with reference to the drawings, wherein like reference numerals identify similar or identical elements. In the drawings and in the description that follows, the term "proximal," will refer to the end of the device that is closest to the operator, while the term "distal" will refer to the end of the device that is farthest from the operator. In addition, the term "cephalad" is used in this application to indicate a direction toward a patient's head, whereas the term "caudad" indicates a direction toward the patient's feet. Further still, for the purposes of this application, the term "medial" indicates a direction toward the middle of the body of the patient, whilst the term "lateral" indicates a direction toward a side of the body of the patient (i.e., away from the middle of the body of the patient). The term "posterior" indicates a direction toward the patient's back, and the term "anterior" indicates a direction toward the patient's front. In the following description, well-known functions or constructions are not described in detail to avoid obscuring the present disclosure in unnecessary detail.

Figure 1B:
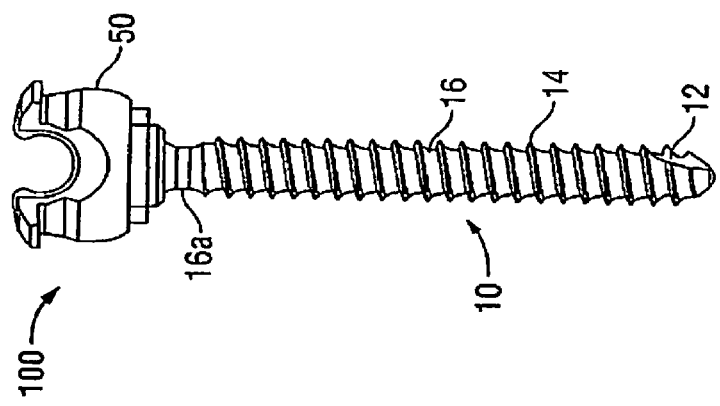
FIG. 1B is a front view of the spinal fixation device of FIG. 1A.
Figure 1A:
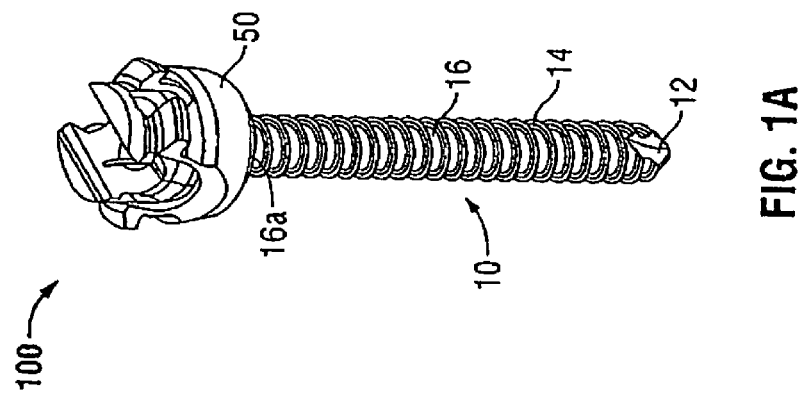
FIG. 1A is a top perspective view of one embodiment of a spinal fixation device having a taper lock.

Referring initially to FIGS. 1A-1C, in which like reference numerals identify similar or identical elements, a spinal fixation device is generally designated as 100. The spinal fixation device 100 includes a pedicle screw 10, a pin 30, an outer housing or coupling 50, and an inner housing or collet 70. One example of such a spinal fixation device is disclosed in International Application Number PCT/US2008/080682, the entire contents of which are hereby incorporated by reference herein.

As shown in FIG. 1C, the pin 30 provides a slidable interconnection between the coupling 50 and the collet 70 such that the coupling 50 and the collet 70 are selectively positionable between an unlocked position and a locked position for locking one or both of the pedicle screw 10 and a rod (not shown). In addition, the pin 30 facilitates an aligned interface between the coupling 50 and the collet 70 such that rotational movement between the coupling 50 and the collet 70 is prevented. In embodiments, the coupling 50 and the collet 70 are configured to lock the pedicle screw 10 while enabling the rod to slide and/or rotate within the collet 70 and/or the coupling 50.

Figure 2A:
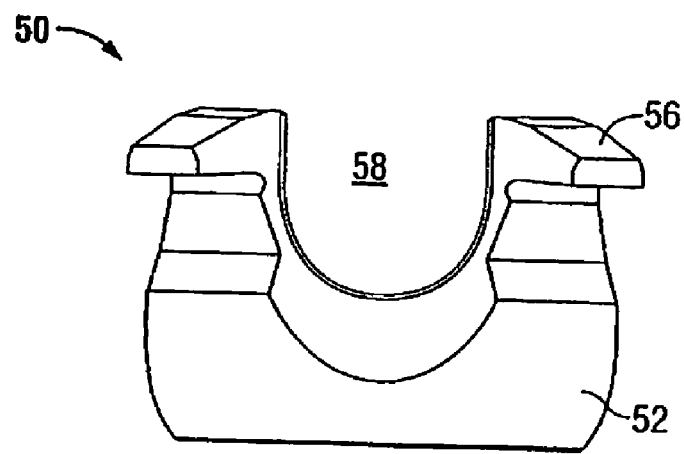
FIG. 2A is a front view of the coupling.
Figure 2B:
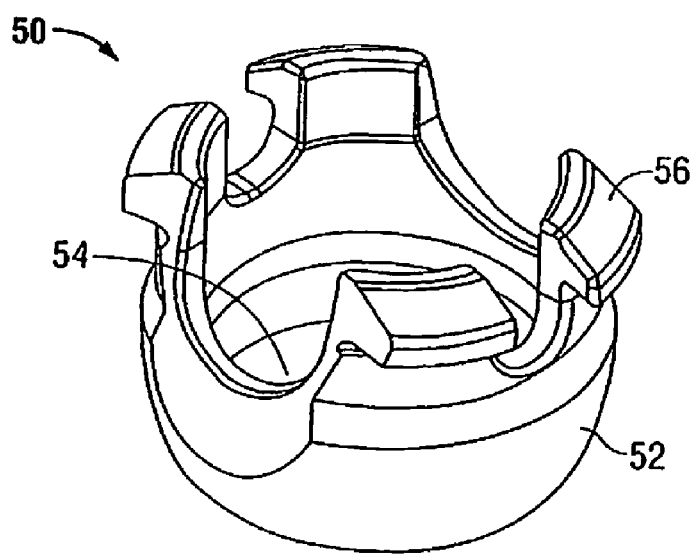
FIG. 2B is a top perspective view of the coupling of FIG. 2A.

Referring now to FIGS. 1C, 2A and 2B, the coupling 50 includes an annular body portion 52 having an opening 54 extending axially therethrough. Additionally, the coupling 50 includes a plurality of fingers 56 that are located in opposing regions of the coupling 50 and define a saddle 58 having a generally U-shaped configuration. The U-shaped saddle 58 is configured and dimensioned for receiving the rod. The coupling 50 includes a pin hole 50p for supporting pin 30 therein.

Figure 3A:
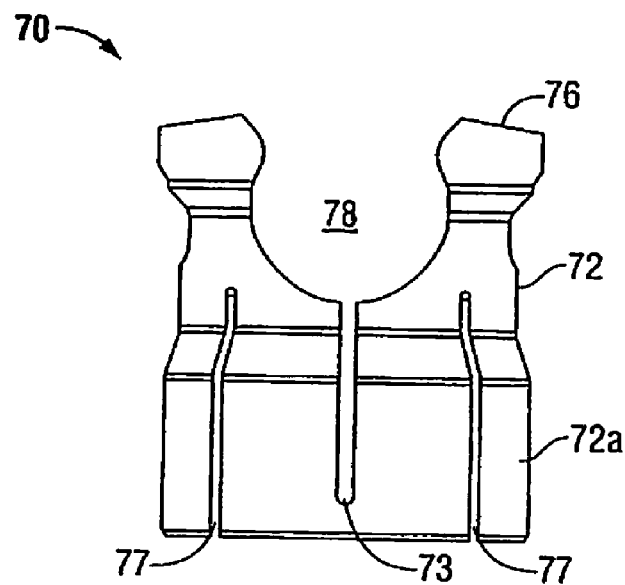
FIG. 3A is a front view of the collet.
Figure 3B:
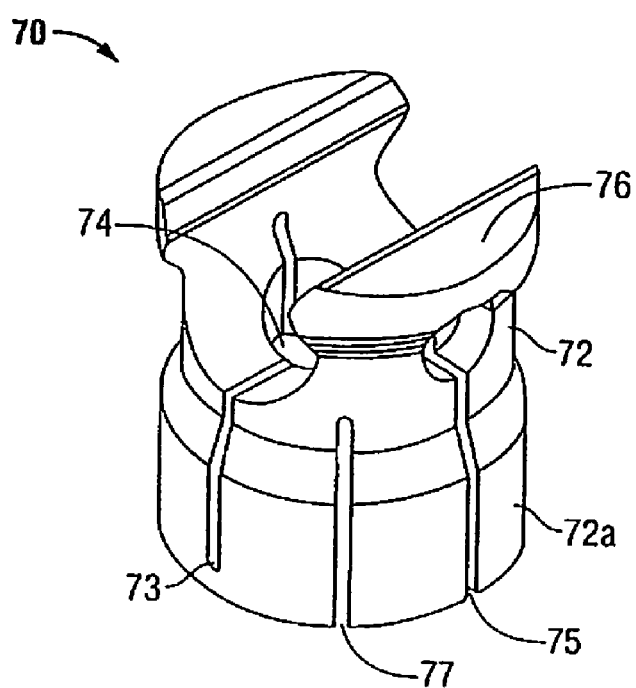
FIG. 3B is a top perspective view of the collet of FIG. 3A.

As shown in 3A and 3B, the collet 70 has a generally cylindrical body portion 72 with an opening 74 extending axially therethrough. A pair of upstanding wings 76 defines a saddle 78 having a generally U-shaped configuration. The saddle 78 is configured and dimensioned for receiving the rod such that the saddle 78 is positionable between a first position where the wings 76 are substantially upstanding and a second position where the wings 76 are angularly displaced from the upstanding position so that the saddle 78 of the collet 70 receives the rod therein. The body portion 72 includes a slot 73 that extends from the nadir of the saddle 78 towards the bottom of the body portion 72 and essentially bisects the body portion 72 along a central axis, and defines left and right sections of the body portion 72 as viewed in FIG. 3A. Preferably, the slot 73 does not extend all the way through the body portion 72. Although less desirable, such a full slot could be used. This arrangement permits each of the wings 76 to flex towards and away from each other. The dimensions of the saddle 78 vary according to the flexure of the wings 76. As the wings 76 are moved closer to each other, the saddle 78 decreases in size and when the wings 76 are moved away from each other, the saddle 78 increases in size. Allowing the saddle 78 to vary in size permits the collet 70 to accommodate rods having differing outside diameters. Alternatively, compressing the wings 76 towards each other increasingly engages the outer surface of the rod located in the saddle 78, thereby frictionally securing the rod in a desired position.

In addition, the body portion 72 includes a plurality of grooves 75 that extend to the bottom of the body portion 72 and which are open at the bottom of the body portion 72. The grooves 75 extend vertically into each of the wings 76, and define front and rear portions of the body portion 72. As configured, the grooves 75 permit the front and rear sections of the body portion 72 to flex relative to the grooves 75 along the axis defined by the slot 73. The body portion 72 also includes a plurality of notches 77 that are open at the bottom surface of the body portion 72 and extend vertically towards the wings 76. The notches 77, in combination with the slot 73 and the grooves 75, allow arcuate sections 72a of the body portion 72 to flex inwards and outwards from an initial position in response to compressive and tensile forces applied to the sections 72a. As best shown in FIG. 1C, the body portion 72 further includes a pin slot 70p for receiving the pin 30 therein so that the body portion 72 of the collet and the coupling 50 are slidably engaged.

Figure 4A:
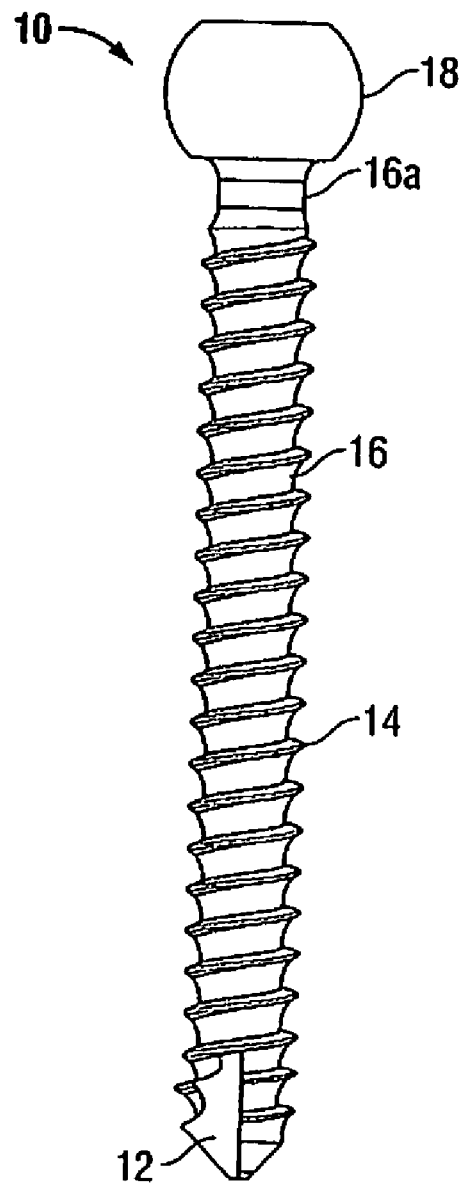
FIG. 4A is a side view of the pedicle screw.
Figure 4B:
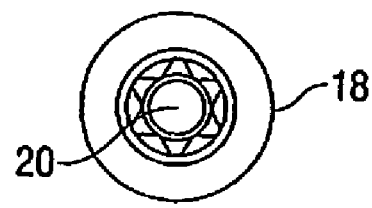
FIG. 4B is a top view of the pedicle screw of FIG. 4A.
Figure 5:
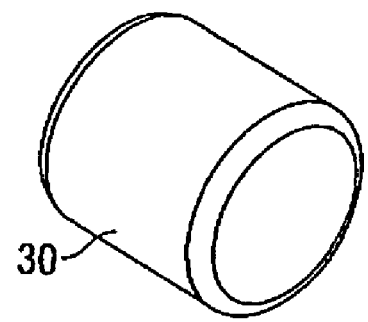
FIG. 5 is a front perspective view of the pin.

Referring now to FIGS. 4A and 4B, the pedicle screw 10 includes a head 18 at the proximal end thereof and a shank 16 at the distal end thereof having a helical thread 14 formed thereon. A cutting portion 12 is formed at a distal end of the shank 16. The head 18 has an outer diameter that is greater than the outer diameter of the shank 16. The head may be spherically shaped. On the top surface of the head 18, a recess 20 is formed. The recess 20 is illustrated with a six-pointed star configuration for receiving the operative end of a suitable driving tool, but it is contemplated that other configurations may be used. A neck 16a extends between a bottom surface of the head 18 and the beginning of the helical thread 14. As configured, the neck 16a is unthreaded. As shown, at least a portion of the diameter of the neck 16a is less than the diameter of the bottom of the head 18 and the major diameter of the threaded portion of the shank 16.

Referring again to FIGS. 1A-1C, the spinal fixation device 100 will now be discussed as assembled for use. The collet 70 is seated atop and engagable with the head 18 of pedicle screw 10. The opening at the bottom of collet 70 is dimensioned and configured for receiving the head 18. As such, the collet 70 and the head 18 are rotatable and pivotable in relation to each other, thereby allowing the pedicle screw 10 to be repositioned in a plurality of orientations relative to the collet 70 for positioning within a vertebral body. The combination of the collet 70 and pedicle screw 10 is inserted into the opening 54 of the coupling 50 which is adapted to receive the collet 70 and the pedicle screw 10 therein. The pin 30 aligns the collet 70 and the coupling 50 for maintaining a fixed relationship between them. As assembled, the pedicle screw 10 is rotatable and pivotable in relation to the collet 70 and the coupling 50 such that when one or more spinal fixation devices 100 are positioned within one or more misaligned vertebral bodies and connected to the rod, the one or more spinal fixation devices 100 and the rod facilitate the interconnection of the misaligned vertebral bodies.

Figure 6:
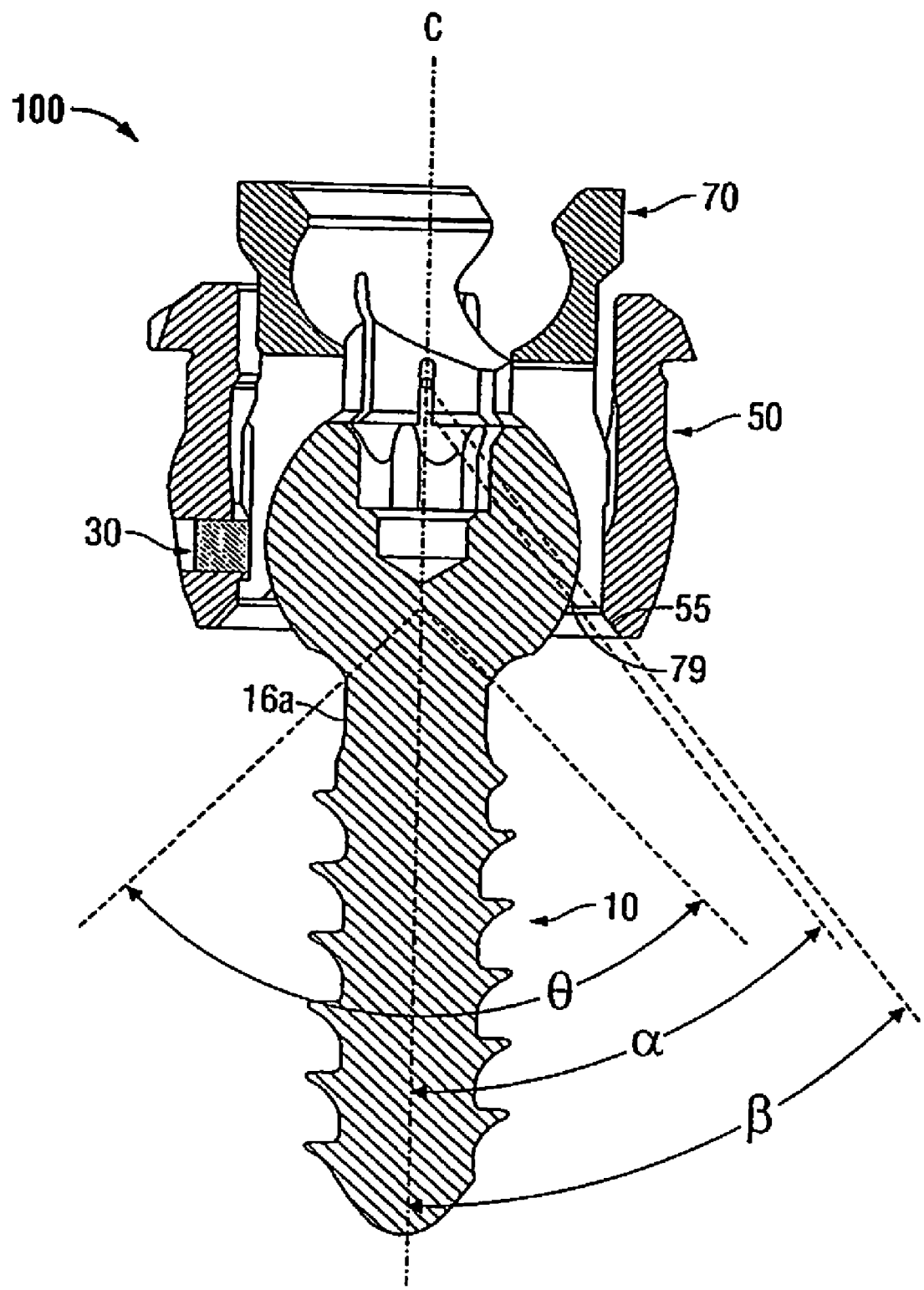
FIG. 6 is a side cross-sectional view of the spinal fixation device of FIG. 1A.

Referring now to FIG. 6, additional features of the assembled spinal fixation device 100 will be discussed. The coupling 50 includes an inner annular lip 55 that is beveled. The lip 55 extends upwards and inwards from a bottom outer edge of the coupling 50. Additionally, the collet 70 includes an annular beveled lip 79 that also extends upwards and inwards from bottom outer edge of the collet 70. As shown in FIG. 6, angle α measures the angle of the beveled lip 79 from centerline C to the beveled lip 79. Angle α may measure between 25 and 65 degrees. In an embodiment, angle α is approximately equal to 45 degrees. Angle β measures the angle of the beveled lip 55 from the centerline C to the beveled lip 55. Angle β may measure between 32 and 72 degrees. In an embodiment, angle β is approximately equal to 52 degrees. By providing the coupling 50 and the collet 70 with beveled lips 55, 79, there is a reduced interaction between the head 18 and the coupling 50 and/or the collet 70. In addition, the pedicle screw 10 has a neck 16a with a length and diameter that cooperate with the beveled lips 55, 79 for reducing interaction therebetween. That is, the length of the non-threaded neck portion 16a of the pedicle screw 10 extends a distance from the bottom of the head 18 to a point beyond the beveled lip 79 of the of the collet 70 and beveled lip 55 of the coupling 50, which together with the selected diameter of the neck 16a permits maximum angular motion of the pedicle screw 10 relative to the collet 70 and coupling 50. This creates a smooth transition zone between the unthreaded neck 16a and the collet 70 and the coupling 50. By reducing the interference between the neck 16a and the beveled lips 55, 79 in combination with the reduced interaction between the head 18 and the beveled lips 55, 79, the pedicle screw 10 defines a cone of at least 70° with respect to a centerline "C" of the spinal fixation device (FIG. 6). In another embodiment, the pedicle screw 10 has a conical range of motion that is at least 90°. In a further embodiment, the pedicle screw 10 has a conical range of motion that is at least 95°.

Specifically, the pedicle screw 10 is capable of being repositioned from a first position (FIG. 6) throughout a plurality of angular positions with respect to the centerline "C". The angular displacement with respect to the centerline "C" is shown as angle θ. Angle θ is at least 70°. In other embodiments, angle θ is in a range between about 80° and about 95°. As such, the pedicle screw 10 moves relative to the centerline "C" (i.e. off axis) in a range of about 35° to about 47.5°.

Figure 7A:
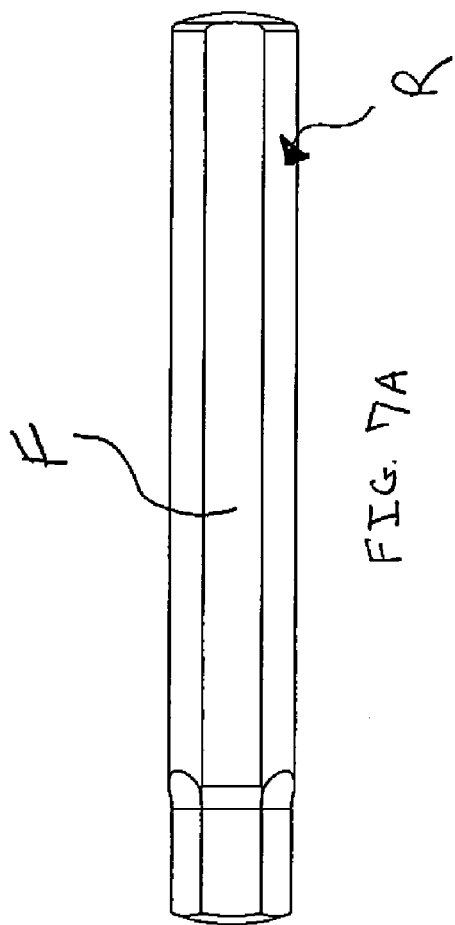
FIG. 7A is top view of one embodiment of a rod.
Figure 7B:
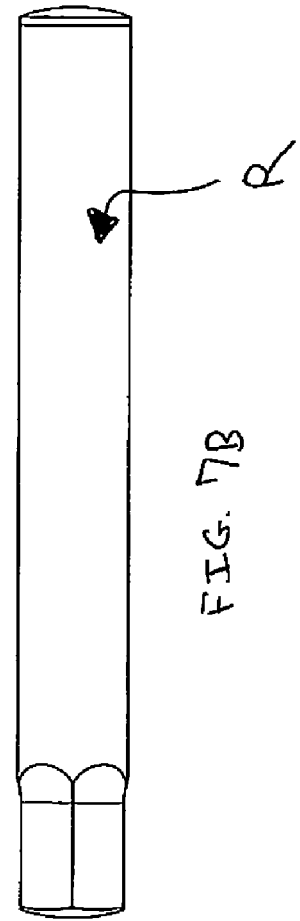
FIG. 7B is a side view of the rod of FIG. 7A.
Figure 7C:
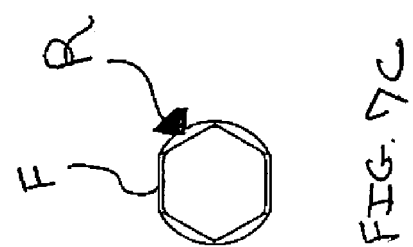
FIG. 7C is an end view of the rod of FIGS. 7A and 7B.
Figure 8B:
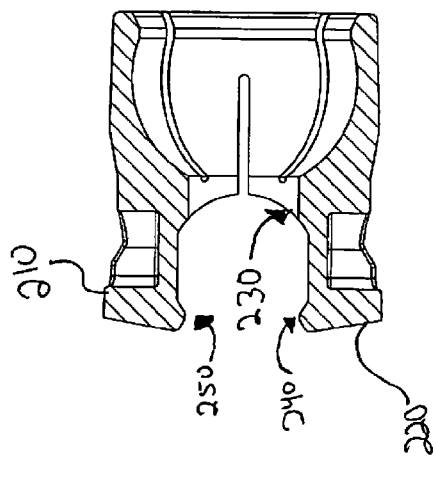
FIG. 8B is a cross-sectional view of the collet of FIG. 8A taken along section line A-A.
Figure 8D:
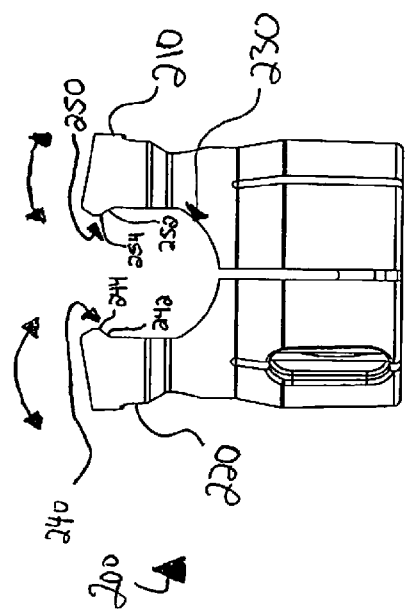
FIG. 8D is a rear view of the collet of FIGS. 8A and 8C.
Figure 8A:
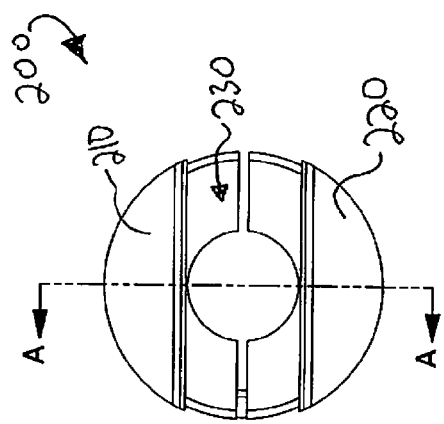
FIG. 8A is a top view of one embodiment of a collet in accordance with the present disclosure.
Figure 8C:
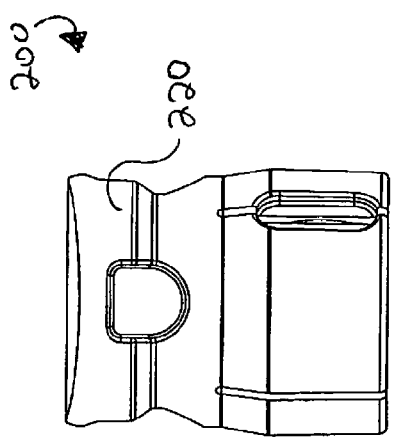
FIG. 8C is a side view of the collet of FIG. 8A.
Figure 9B:
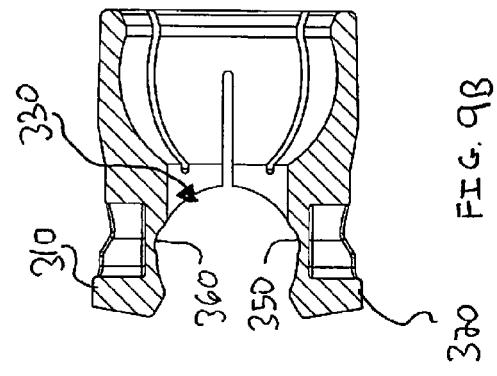
FIG. 9B is a cross-sectional view of the collet of FIG. 9A taken along section line B-B.
Figure 9D:
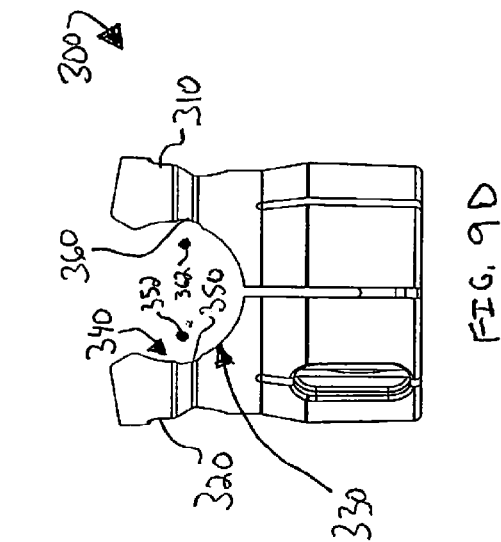
FIG. 9D is a rear view of the collet of FIGS. 9A and 9C.
Figure 9A:
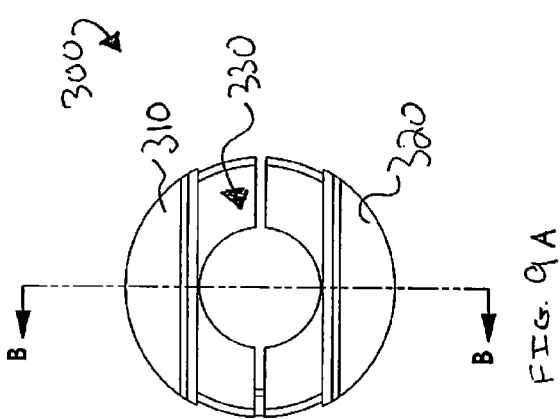
FIG. 9A is a top view of one embodiment of a collet in accordance with the present disclosure.
Figure 9C:
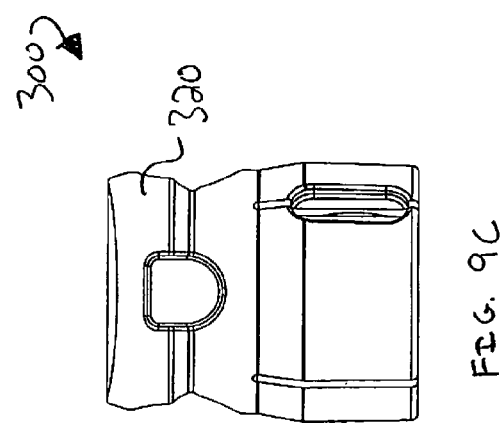
FIG. 9C is a side view of the collet of FIG. 9A.
Figure 10A:
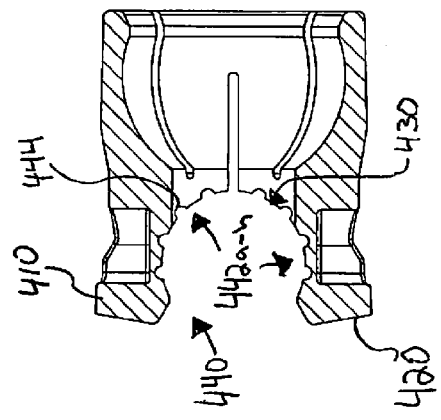
FIG. 10A is a top view of one embodiment of a collet in accordance with the present disclosure.
Figure 10B:
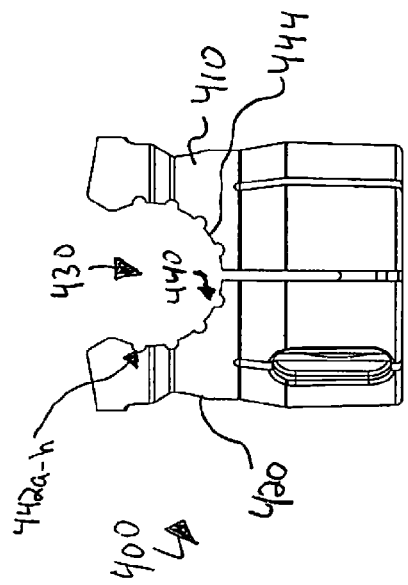
FIG. 10B is a cross-sectional view of the collet of FIG. 10A taken along section line D-D.
Figure 10C:
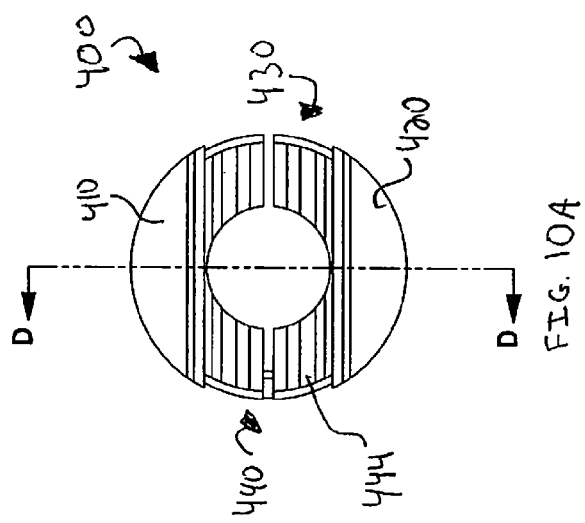
FIG. 10C is a side view of the collet of FIG. 10A.
Figure 10D:
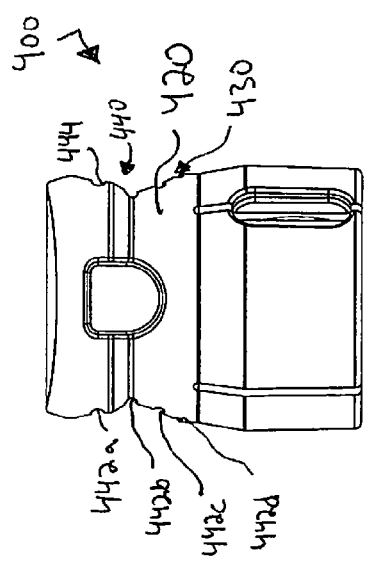
FIG. 10D is a rear view of the collet of FIGS. 10A and 10C.
Figure 11B:
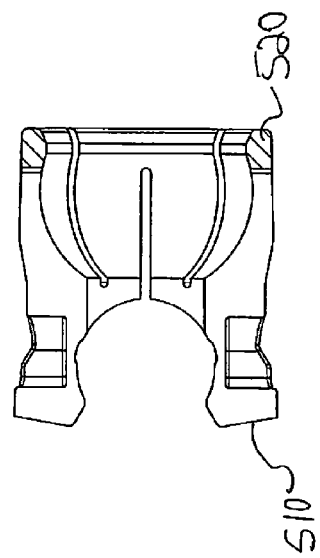
FIG. 11B is a cross-sectional view of the collet of FIG. 11A taken along section line F-F.
Figure 11D:
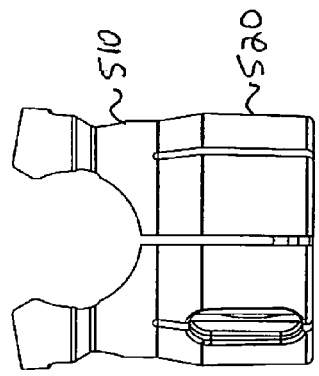
FIG. 11D is a rear view of the collet of FIGS. 11A and 11C.
Figure 11A:
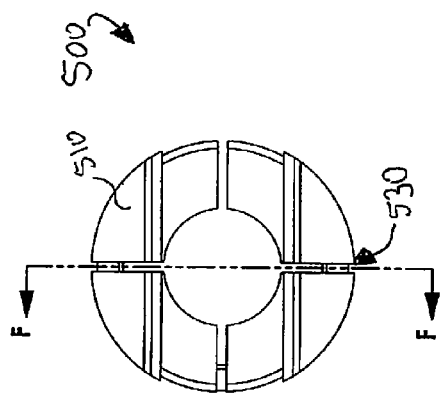
FIG. 11A is a top view of one embodiment of a collet in accordance with the present disclosure.
Figure 11C:
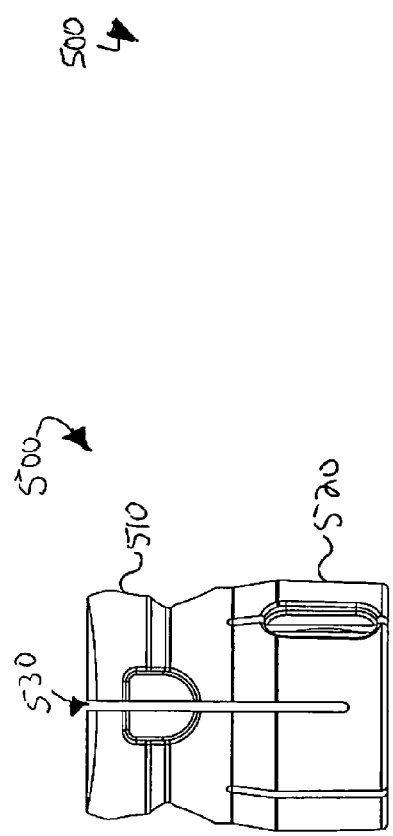
FIG. 11C is a side view of the collet of FIG. 11A.

With reference to FIGS. 7A-7C, one embodiment of a spinal rod is illustrated and is generally designated "R." The spinal rod "R" has an elongate body, and in this embodiment, the spinal rod "R" includes one or more flat surfaces "F" for engaging a collet. The one or more flat surfaces "F" facilitate increased rod friction with the collet for preventing axial and/or rotational movement of the spinal rod "R" within the collet.

Referring now to FIGS. 8A-8D, one embodiment of a collet 200 is substantially similar to collet 70 described above. However, collet 200 includes a pair of upstanding wings 210, 220 that defines a saddle 230 having a generally U-shaped configuration and one or more locking features 240, 250 thereon for engaging the spinal rod "R." The one or more locking features 240, 250 include one or both of a flat edge 242, 252 or a corner 244, 254.

With reference to FIGS. 7A-8D, the one or more flat surfaces "F" of the spinal rod "R" (FIGS. 7A-7C) are adapted to lockingly engage with the one or more locking features 240, 250 of the collet 200. In this manner, the engagement between the one or more flat surfaces "F" of the spinal rod "R" and the one or more locking features 240, 250 of the collet 200 prevent the spinal rod "R" from axially and/or rotationally moving within the saddle 230 of the collet 200. In particular, the flat edge 242, 252 and/or the corner 244, 254 of the one or more locking features 240, 250 facilitate the locking engagement by inhibiting the rotational movement of the spinal rod "R" via the engagement with the flat surfaces "F." In addition, the flat surfaces "F" engage the flat edge 242, 252 of the one or more locking features 240, 250 such that there is increased friction in the axial direction between the surfaces thereof for limiting and/or preventing axial translation.

With continued reference to FIGS. 8A-8D, the collet 200 is positionable between a first position where the wings 210, 220 are substantially upstanding and a second position where the wings 210, 220 are angularly displaced or flexed, inwardly and/or outwardly, from the upstanding position so that the saddle 230 of the collet 200 receives the spinal rod "R" therein. In the second position, the one or more flat surfaces "F" are in locking engagement with the one or more locking features 240, 250 of the collet 200 for preventing the rotational and/or axial movement of spinal rod "R" within the saddle 230 as described above.

As illustrated in FIGS. 9A-9D, a collet 300 is substantially similar to collet 200 described above. However, collet 300 includes a pair of upstanding wings 310, 320 that defines a saddle 330 having a generally U-shaped configuration and a locking feature 340. The locking feature 340 includes slots 350, 360 defined within the surface of the saddle 330. In this embodiment, a rod, which may be circular, is positioned within the saddle 330 and engaged by slots 350, 360 such that the slots 350, 360 prevent rotational and/or axial movement of the circular rod within the saddle 330. Each slot 350, 360 has a radius defined by a center point 352, 362. The center points 352, 362 of each slot 350, 360 are not coincidental. The non-coincidental center points 352, 362 increase the interference between the saddle 330 and the rod, increasing the grip on the rod.

As illustrated in FIGS. 10A-10D, a collet 400 is substantially similar to collet 300 described above. However, collet 400 includes a pair of upstanding wings 410, 420 that defines a saddle 430 having a generally U-shaped configuration and a locking feature 440. In this embodiment, the locking feature 440 includes a plurality of scallops 442a-442h that define a scalloped surface 444. This embodiment represents a macro-finish or surface texturing which significantly increase the frictional component between the rod and the spinal fixation device. The force on the rod per scallop is inversely proportional to the number of scallops 442a-442h. In other words, as the number of scallops increases, the amount of force each scallop asserts onto the rod decreases.

Referring now to FIGS. 11A-11D, a collet 500 is substantially similar to collet 300 described above. Collet 500 includes an upper portion 510 and a lower portion 520 and one or more relief slots 530 disposed within one or both of the upper portion 510 and the lower portion 520. The relief slots 530 facilitate the deformity of the collet 500 and thereby providing an increase in rod capturing frictional forces for preventing rotational and/or axial movement of the rod. The relief slots 530 may be any number, suitable shape or dimension to facilitate the flexibility or promote the rigidity of the collet 500.

In embodiments, the saddle of the collet may include surface texturing to increase fixation between the spinal fixation device and the rod. Such surface texturing may include, but is not limited to, plasma spray, bead blasting, porous coating, macro-texturing, spikes, or other surface protrusions that may penetrate the rod surface to increase the slip and grip strength between the spinal fixation device and the rod.

It will be understood that various modifications may be made to the embodiments of the presently disclosed device. Therefore, the above description should not be construed as limiting, but merely as exemplifications of embodiments. Those skilled in the art will envision other modifications within the scope and spirit of the present disclosure.

What is claimed is:

1. A spinal fixation device, comprising:
a coupling having an opening extending therethrough;
a pedicle screw having a head mounted to a shank, the shank positionable within a first vertebral body; and
a collet receivable in the opening of the coupling and engagable with the head of the pedicle screw, the collet selectively positionable between a first position and a second position where the collet engages a spinal rod and prevents at least one of axial and rotational movement of the spinal rod, the collet adapted to facilitate connection of the spinal rod to a second vertebral body, the collet defining a saddle, the saddle defining at least two locking features within a surface of the saddle for engaging the spinal rod, each locking feature having a radius defined by a center point, the center points of the at least two locking features being non-coincidental, the coupling and the collet being configured to lock the pedicle screw while enabling the spinal rod to slide and/or rotate within the collet and/or the coupling when the coupling and the collet are positioned in a partially locked condition.

2. The spinal fixation of claim 1, wherein the collet facilitates the connection of the spinal rod to the second vertebral body misaligned with respect to the first vertebral body when the collet is in the second position.

3. The spinal fixation device of claim 1, wherein the saddle includes a plurality of locking features.

4. The spinal fixation device of claim 3, wherein the plurality of locking features defines a scalloped surface.

5. The spinal fixation device of claim 3, wherein the plurality of locking features includes a first locking feature and a second locking feature, the saddle defining a U-shaped opening in both the first and second positions, the spinal rod being positionable within the U-shaped opening, the first locking feature substantially facing the second locking feature across the U-shaped opening of the saddle.

6. The spinal fixation device of claim 3, wherein the coupling defines a longitudinal axis that extends between leading and trailing ends of the coupling, the at least two locking features being longitudinally offset relative to one another.

7. The spinal fixation device of claim 1, wherein the at least one locking feature includes a slot defined within the surface of the saddle.

8. The spinal fixation device of claim 1, wherein the collet includes at least one relief slot.

9. The spinal fixation device of claim 1, wherein the collet includes an upper portion and a lower portion, wherein the at least one relief slot is disposed within at least one of the upper portion and the lower portion.

10. The spinal fixation device of claim 1, wherein the at least one locking feature includes at least one of a flat edge or a corner.

11. The spinal fixation device of claim 1, wherein the saddle of the collet includes surface texturing.

12. A spinal fixation assembly, comprising:
a spinal rod having at least one flat surface; and
a spinal fixation device, comprising:
a coupling having an opening extending therethrough;
a pedicle screw having a head mounted to a shank, the shank positionable within a first vertebral body; and
a collet receivable in the opening of the coupling and engagable with the head of the pedicle screw, the collet selectively positionable between a first position and a second position where the collet engages a spinal rod and prevents at least one of axial and rotational movement of the spinal rod, the collet adapted to facilitate connection of the spinal rod to a second vertebral body, the collet defining a saddle, the saddle defining at least two locking features within a surface of the saddle for engaging the at least one flat surface of the spinal rod, each locking feature having a radius defined by a center point, the center points of the at least two locking features being non-coincidental, the coupling and the collet being configured to lock the pedicle screw while enabling the spinal rod to slide and/or rotate within the collet and/or the coupling when the coupling and the collet are positioned in a partially locked condition.

13. The spinal fixation assembly of claim 12, further comprising a second spinal fixation device positionable within the second vertebral body and engagable with the spinal rod.

14. A spinal fixation device, comprising:
a coupling having an opening extending therethrough;
a pedicle screw having a head mounted to a shank, the shank positionable within a first vertebral body; and
a collet receivable in the opening of the coupling and engagable with the head of the pedicle screw, at least one of the coupling and the collet being movable relative to the other of the coupling and the collet in a taper lock arrangement to selectively position the collet-between an unlocked position and a locked position, the collet engaging a spinal rod and preventing at least one of axial and rotational movement of the spinal rod in the locked position, the collet facilitating connection of the spinal rod to a second vertebral body and defining a saddle, the saddle defining at least two locking features within a surface of the saddle for engaging the spinal rod, each locking feature having a radius defined by a center point, the center points of the at least two locking features being non-coincidental, the coupling and the collet being configured to lock the pedicle screw while enabling the spinal rod to slide and/or rotate within the collet and/or the coupling when the coupling and the collet are positioned in a partially locked condition.

15. The spinal fixation device of claim 14, wherein the saddle includes a plurality of locking features.

16. The spinal fixation device of claim 15, wherein the plurality of locking features includes a first locking feature and a second locking feature, the saddle defining a U-shaped opening in both the unlocked and locked positions, the spinal rod being positionable within the U-shaped opening, the first locking feature substantially facing the second locking feature across the U-shaped opening of the saddle.

17. The spinal fixation device of claim 15, wherein at least two locking features are defined within the surface of the saddle and each locking feature has a radius defined by a center point, wherein the center points are non-coincidental.

18. The spinal fixation device of claim 17, wherein the coupling defines a longitudinal axis that extends between leading and trailing ends of the coupling, the at least two locking features being longitudinally offset relative to one another.

* * * * *